United States Patent
Bos et al.

(10) Patent No.: US 10,201,160 B2
(45) Date of Patent: Feb. 12, 2019

(54) ANTIMICROBIAL COMPOSITION FOR PROTECTING WOOD

(71) Applicant: Bos Holdings Inc., Strathroy (CA)

(72) Inventors: Eric Bos, London (CA); Nenad Vidovic, Toronto (CA)

(73) Assignee: Boss Holdings Inc., Strathroy (CA)

( * ) Notice: Subject to any disclaimer, the term of this patent is extended or adjusted under 35 U.S.C. 154(b) by 0 days.

(21) Appl. No.: 15/312,549

(22) PCT Filed: May 20, 2015

(86) PCT No.: PCT/CA2015/000356
§ 371 (c)(1),
(2) Date: Nov. 18, 2016

(87) PCT Pub. No.: WO2015/176171
PCT Pub. Date: Nov. 26, 2015

(65) Prior Publication Data
US 2017/0112133 A1 Apr. 27, 2017

(30) Foreign Application Priority Data
May 21, 2014 (CA) ...................... 2852530

(51) Int. Cl.
*A01N 25/04* (2006.01)
*A01N 47/18* (2006.01)
(Continued)

(52) U.S. Cl.
CPC ............. *A01N 47/18* (2013.01); *A01N 25/04* (2013.01); *A01N 43/653* (2013.01); *A01N 47/12* (2013.01);
(Continued)

(58) Field of Classification Search
CPC ...... A01N 25/04; B27K 2240/20; B27K 3/50; C09D 5/024; C09D 5/14
See application file for complete search history.

(56) References Cited

U.S. PATENT DOCUMENTS

| | | |
|---|---|---|
| 4,079,062 A | 3/1978 | Van Reet et al. |
| 4,732,905 A | 3/1988 | Donofrio et al. |

(Continued)

FOREIGN PATENT DOCUMENTS

| | | |
|---|---|---|
| CA | 2338569 A1 | 2/2000 |
| WO | 9601054 A1 | 1/1996 |

(Continued)

OTHER PUBLICATIONS

Wozniak et al. (International Research Group on Wood Protection Conference, May 19, 2000—provided by Applicant in the IDS of Sep. 21, 2017).*

(Continued)

*Primary Examiner* — Valerie Rodriguez-Garcia
(74) *Attorney, Agent, or Firm* — Erickson Kernell IP, LLC

(57) ABSTRACT

A multifunctional broad spectrum antimicrobial composition is described. The composition can be incorporated into a wood preservative, or used as an additive to provide antimicrobial properties to water-based wood coatings. The composition is a concentrated water-miscible emulsion containing 3-iodo-2-propynyl N-butylcarbamate (IPBC), carbendazim (BCM) and propiconazole (PPCZ), and has antimicrobial activity against a wide variety of fungal organisms, including surface molds, blue stain fungi and wood rotting fungi. The composition can act as an in-can preservative and is useful for antimicrobial protection of wood and wood-based substrates.

20 Claims, 6 Drawing Sheets
(5 of 6 Drawing Sheet(s) Filed in Color)

(51) Int. Cl.
*C09D 5/02* (2006.01)
*B27K 3/50* (2006.01)
*C09D 5/14* (2006.01)
*A01N 43/653* (2006.01)
*B27K 3/36* (2006.01)
*B27K 3/34* (2006.01)
*A01N 47/12* (2006.01)
*C09D 7/63* (2018.01)
*C08K 5/00* (2006.01)

(52) U.S. Cl.
CPC ............... *B27K 3/343* (2013.01); *B27K 3/36* (2013.01); *B27K 3/50* (2013.01); *C09D 5/024* (2013.01); *C09D 5/025* (2013.01); *C09D 5/14* (2013.01); *C09D 7/63* (2018.01); *B27K 3/34* (2013.01); *B27K 2240/20* (2013.01); *C08K 5/0058* (2013.01)

(56) References Cited

U.S. PATENT DOCUMENTS

| | | | |
|---|---|---|---|
| 5,098,472 A * | 3/1992 | Watkins | C09D 15/00 106/123.12 |
| 5,326,777 A | 7/1994 | Ludwig et al. | |
| 5,385,926 A | 1/1995 | Ludwig et al. | |
| 5,631,273 A | 5/1997 | Merianos | |
| 6,197,805 B1 | 3/2001 | Smith | |
| 6,372,771 B1 | 4/2002 | Ludwig et al. | |
| 6,558,685 B1 | 5/2003 | Kober et al. | |
| 6,849,664 B2 | 2/2005 | O'Reilly et al. | |
| 7,993,756 B2 | 8/2011 | Jin et al. | |
| 2005/0084471 A1 * | 4/2005 | Andrews | A01N 37/12 424/70.31 |
| 2006/0013847 A1 | 1/2006 | Bartko | |
| 2006/0251915 A1 | 11/2006 | Jin et al. | |
| 2008/0096763 A1 * | 4/2008 | Dawson | A01N 25/30 504/206 |
| 2009/0192219 A1 | 7/2009 | Uhr et al. | |
| 2009/0258916 A1 * | 10/2009 | Felder | A01N 43/80 514/372 |
| 2010/0286217 A1 * | 11/2010 | Annis | A01N 25/02 514/372 |
| 2011/0015299 A1 * | 1/2011 | Annis | C09D 5/025 523/122 |

FOREIGN PATENT DOCUMENTS

| | | |
|---|---|---|
| WO | 9627483 A1 | 9/1996 |
| WO | 0208372 A1 | 1/2002 |
| WO | 2009091450 A1 | 7/2009 |

OTHER PUBLICATIONS

ICI Americas Inc. ("The HLB System a time saving guide to emulsifier selection" edited and reprinted from Chemmunique, Mar. 1980).*

Wozniak, "Xylophene ASTM, the challenge of developing a modern antisapstain formulation for the French market" International Research Group on Wood Protection Conference, May 19, 2000. Retrieved from the Internet on Aug. 17, 2015: http://www.irg-wp.com/irgdocs/details.php?7f9d97d1-6dcb-4598-95e3-55035ea2a78f.

CTBA, "Produits de traitement temporaires des sciages frais". CTBA, Jul. 5, 2012, 3rd sub-document, pp. 3/3. Retrieved from the Internet on Aug. 17, 2015: http://www.holzfragen.de/pdf/CTBA%20P+%20liste%20produits.pdf.

* cited by examiner

ANTIMICROBIAL COMPOSITION FOR PROTECTING WOOD

BACKGROUND

The present application is directed to an antimicrobial composition for protecting wood. More specifically, the present application is directed to a multifunctional broad spectrum antimicrobial composition which can be incorporated into a wood preservative, or can be used as an antimicrobial additive in water-based wood and wood composite coatings.

Wood surfaces, such as those on buildings and other structures which are exposed to the environment, are susceptible to attack by microbes such as fungi or bacteria and other pests. For example, in areas such as the Lower Mainland of British Columbia, mold growth on attic roof components, especially on wood framing and sheathing, can occur because of roof leaks or water vapor condensation. When air-borne fungal spores and/or tiny air-borne mycelia fragments land on wet or damp wood surfaces, initial mold culture can become established and later proliferate into large colonies. Attempts to prevent the significant condensation problem in such areas by re-designing roofs have not so far successfully addressed the issue.

Fungal attack of wood surfaces can compromise or destroy the structural integrity of the wood, as well as damage its appearance. As well, mold colonies can release high levels of mycotoxins to prevent invasion by competitive organisms. As a result, apart from cosmetic problems, mold growth can cause adverse health effects in humans, and considerably reduce the commercial value of structures.

Coatings and preservatives for such wood surfaces therefore often include antimicrobial compounds to protect the wood from damage caused by such microbes. A wide variety of antimicrobial compounds are known to be used in such wood preservatives and coatings. However, in many cases, such antimicrobial compounds are less effective against some species than others, and may need to be present at relatively high levels to have broad spectrum effectiveness against an adequate range of microbes. Alternatively, combinations of individual antimicrobial products, each of which individually has effectiveness against a specific species or groups of species, may be necessary to achieve broad spectrum effectiveness against the desired range of microbes.

For some applications of wood coatings, it is desirable that such antimicrobial compounds be present at low levels or absent. Many such antimicrobial compounds can be harmful to humans or animals. Thus, if it is likely that humans or animals will come into contact with a coated wood surface, it is desirable to prevent or minimize exposure to potentially harmful levels of antimicrobial compounds caused by such contact. Furthermore, in some cases, wood surfaces may not be exposed to an environment where attack by microbes is a substantial risk, and therefore would not need a high level of antimicrobial protection. In such cases, there would be no need to risk exposing users to high levels of antimicrobial compounds during application of a coating. Thus, manufacturers who wish to provide a choice of coatings to their customers must develop a number of different antimicrobial or non-antimicrobial formulations at additional effort and cost.

Therefore, there is a need for an antimicrobial composition which can be conveniently stored and diluted as needed to provide a wood preservative, or which can be added to wood preservative and wood coating formulations so as to provide the formulations with antimicrobial properties as desired. In this way, coating manufacturers can readily achieve alternative antimicrobial protection for existing coatings without the need for costly or time-intensive research. In some cases, non-antimicrobial coatings, such as interior paints and stains, could be readily adapted for applications requiring antimicrobial properties.

In addition, it is desirable to provide an antimicrobial composition which has antimicrobial activity against a range of wood-attacking microbes, so as to reduce the need for treatment with multiple products, each containing individual antimicrobial agents.

SUMMARY

In one aspect, the present invention provides an antimicrobial composition, containing from about 10% to about 25% by weight of 3-iodo-2-propynyl N-butyl carbamate (IPBC), about 12% to about 20% by weight of propiconazole (PPCZ), about 2% to about 8% by weight of carbendazim (BCM) and about 25% to about 70% by weight of a carrier fluid. The antimicrobial composition is in the form of an emulsion. In at least one embodiment, the antimicrobial composition further contains about 7% to about 15% by weight of an emulsifier. In at least one embodiment, the antimicrobial composition further contains about 2% to about 4% by weight of a co-emulsifier. In at least one embodiment, the antimicrobial composition further contains about 3% to about 14% by weight of an emulsion stabilizer. In at least one embodiment, the antimicrobial composition further contains about 0.3% to about 3% by weight of an antifoaming agent.

In another aspect, the present invention provides an antimicrobial wood preservative comprising an antimicrobial composition as described herein.

Another aspect of the present invention provides a method of preserving wood, comprising treating the wood with an antimicrobial wood preservative as described herein.

A further aspect of the present invention provides the use of an antimicrobial composition as described herein in the preparation of an antimicrobial wood coating product comprising a water-based wood coating.

In another aspect, the present invention provides a method of preparing an antimicrobial wood coating product comprising adding the antimicrobial composition as described herein to a water-based wood coating to form a mixture; and agitating the mixture to form the antimicrobial wood coating product.

Yet another aspect of the present invention provides an antimicrobial wood coating product comprising a water-based wood coating and an antimicrobial composition as described herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Further features of the present invention will become apparent from the following written description and the accompanying figures, in which.

DETAILED DESCRIPTION

Figure 1:
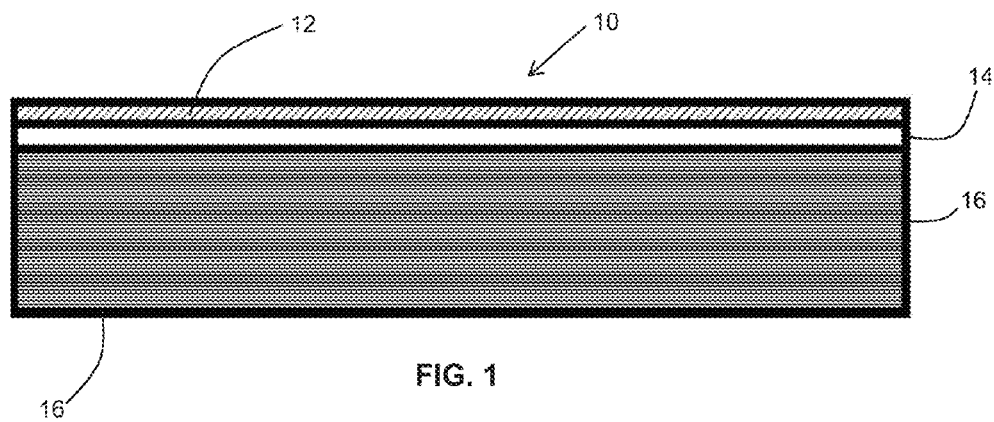
FIG. 1 is a diagram illustrating wood coated with a wood coating from which antimicrobial agents have partially penetrated into the wood.

One aspect of the present invention provides an antimicrobial composition for use in protecting wood from attack by microbes such as fungi and bacteria. As used herein, the term "antimicrobial" is intended to mean a compound or mixture of compounds, including but not limited to a microbicide or microbiocide, which is an agent effective to kill, or to reduce or prevent the growth of, or infection by, one or more living microorganisms, including but not limited to bacteria and fungi. An antimicrobial substance includes but is not limited to a bactericide, bacteriostat, or antibacterial substance, and a fungicide, fungistat or antifungal substance.

In at least one embodiment, the antimicrobial composition has a higher concentration of active antimicrobial ingredients than the minimum necessary for antimicrobial effectiveness. Thus, the antimicrobial composition can be diluted while still retaining antimicrobial efficacy. The antimicrobial composition is useful as an additive to water-based wood coatings, so as to provide the wood coating with antimicrobial properties and/or increase the antimicrobial effectiveness of the wood coating. The antimicrobial composition can also be formulated as an antimicrobial wood preservative or an antimicrobial wood preservative concentrate as described below. The antimicrobial wood preservative concentrate can be diluted with water to prepare an antimicrobial wood preservative formulation having a desired concentration of active ingredients.

In at least one embodiment, the antimicrobial composition is a stable water-miscible suspoemulsion containing three active antimicrobial ingredients: 3-iodo-2-propynyl N-butyl carbamate (IPBC), propiconazole (PPCZ) and carbendazim (BCM). In at least one embodiment, the antimicrobial composition has one or more of the following desirable properties: stable, flowable, having low levels of volatile organic compounds (VOC), low foaming, having low odor. In at least one embodiment, the antimicrobial composition can be formulated into water-based wood preservatives or water-based wood coatings.

The antimicrobial composition can be used for antimicrobial protection of wood substrates, including but not limited to wood substrates which are wet or at risk of being wet. Suitable wood substrates include but are not limited to wet, green logs, freshly sawn lumber, dried solid wood, previously installed wood, engineered wood, and wood composite products, including but not limited to sheathing materials such as oriented strand board (OSB) or plywood. Such antimicrobial protection can include prevention of microbial infection of uninfected wood substrates and treatment of sound wood substrates exposed to microbial infection from which damaged, rotten or infected material has been mechanically or physically removed. In at least one embodiment, the antimicrobial composition can be used for antimicrobial protection of new wood substrates prior to or immediately after installation. In at least one embodiment, the antimicrobial composition can be used for in situ antimicrobial protection of sound wood substrates in existing installations. In at least one embodiment, the antimicrobial composition can be used for remedial antimicrobial protection of sound wood substrates in existing installations where the sound wood substrate has been attacked, or is at risk of being attacked, by microbes. Such remedial protection can include mechanical or physical removal of fungal colonies and removal and/or replacement of damaged, rotten or infected wood substrate material in combination with application of the antimicrobial composition to sound and/or new wood substrate.

The present antimicrobial composition comprises from about 10% to about 25% by weight of 3-iodo-2-propynyl N-butyl carbamate (IPBC), about 12% to about 20% by weight of propiconazole and about 2% to about 8% by weight of carbendazim, as active antimicrobial ingredients. In at least one embodiment, the antimicrobial composition comprises from about 15% to about 20% by weight of IPBC, about 13% to about 17% by weight of propiconazole and about 3% to about 5% by weight of carbendazim. IPBC has the following structural formula:

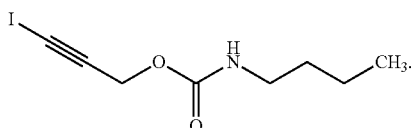

Propiconazole (PPCZ), also known as 1(2-(2,4-dichlorophenyl)-4-propyl-1,3-dioxolan-2-yl)-methyl)-1H-1,2,4-triazole, has the following structural formula:

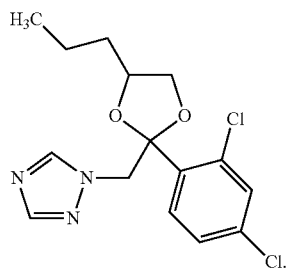 [SMILES: CCCC1COC(Cn2cncn2)(c2ccc(Cl)cc2Cl)O1]

Carbendazim (BCM), also known as methyl benzimidazole-2-yl carbamate, has the following structural formula:

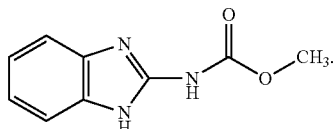

In at least one embodiment, the antimicrobial composition contains a ratio by weight of IPBC:PPCZ:BCM of about 20:20:10. In at least one embodiment, the antimicrobial composition contains a ratio by weight of IPBC:PPCZ:BCM of about 19:19:5. In at least one embodiment, the antimicrobial composition contains a ratio by weight of IPBC:PPCZ:BCM of about 15:14:4. In at least one embodiment, the antimicrobial composition contains from about 24% to about 53% by weight of total active antimicrobial ingredients (IPBC, PPCZ and BCM). In at least one embodiment, the antimicrobial composition contains from about 32% to about 40% by weight of total active antimicrobial ingredients.

In at least one embodiment, the IPBC and BCM are present in solid form and are dispersed in the antimicrobial composition as finite particles. In at least one embodiment, the particles have a particle size from about 0.1 µm to about 10 µm. In at least one embodiment, the particles have a particle size from about 10 µm to about 35 µm. In at least one embodiment, the particles have a particle size from about 13 µm to about 20 µm.

In at least one embodiment, the antimicrobial composition further comprises an emulsion stabilizer. In at least one embodiment, the emulsion stabilizer is a natural or synthetic mineral, including but not limited to clay-based minerals or clay mineral derivatives, such as kaolin, Laponite™ RD or Laponite™ RDS (Rockwood Specialties), bentonite, or bentonite containing montmorillonite. Without being bound by theory, it is believed that the emulsion stabilizer aids in stabilizing the emulsion of the active ingredients in the antimicrobial composition. The skilled person would be aware of other suitable emulsion stabilizers. In at least one embodiment, the composition comprises from about 3% to about 14% by weight of the emulsion stabilizer. In at least one embodiment, the composition comprises from about 5% to about 12% by weight of the emulsion stabilizer.

In at least one embodiment, the antimicrobial composition further comprises an emulsifier. In at least one embodiment, the emulsifier is a non-ionic surfactant. In at least one embodiment, the non-ionic surfactant is an ethoxylated castor oil. In at least one embodiment, the ethoxylated castor oil contains 30 to 40 ethylene oxide units per molecule of castor oil. In at least one embodiment, the ethoxylated castor oil has a Hydrophilic-Lipophilic Balance (HLB) of about 10 to about 14. In at least one embodiment, the non-ionic surfactant is T-DET™ C-40 or T-DET™ BP-1 (Harcros Chemicals Inc.) or HCO-25 (Ethox Chemicals). In at least one embodiment, the emulsifier is an ionic surfactant. In at least one embodiment, the ionic surfactant is an anionic surfactant. In at least one embodiment, the anionic surfactant is E-Sperse™ 100 (Ethox Chemicals). The person of skill in the art would be aware of other suitable emulsifiers.

In at least one embodiment, the antimicrobial composition comprises about 7% to about 15% by weight of the emulsifier. In at least one embodiment, the antimicrobial composition comprises about 10% to about 15% by weight of the emulsifier. In at least one embodiment, the antimicrobial composition comprises about 7% to about 12% by weight of the emulsifier. In at least one embodiment, the antimicrobial composition comprises about 10% by weight of the emulsifier.

In at least one embodiment, the antimicrobial composition further comprises about 2% to about 4% by weight of a co-emulsifier. In at least one embodiment, the antimicrobial composition further comprises about 3% to about 3.5% by weight of a co-emulsifier. In at least one embodiment, the co-emulsifier comprises at least one non-ionic surfactant. In at least one embodiment, the co-emulsifier comprises a plurality of non-ionic surfactants.

In at least one embodiment, the co-emulsifier comprises a first non-ionic surfactant having a low Hydrophilic-Lipophilic Balance (HLB). In at least one embodiment, the first non-ionic surfactant is relatively lipophilic and can favour the formation of water-in-oil emulsions. Suitable first non-ionic surfactants include but are not limited to sorbitan oleate, sorbitan monooleate, Span™ 80, Arlacel™ 80, and Emulsifier S80.

In at least one embodiment, the co-emulsifier further comprises a second non-ionic surfactant having a high HLB. In at least one embodiment, the second non-ionic surfactant is relatively hydrophilic and can favour the formation of oil-in-water emulsions. Suitable second non-ionic surfactants include but are not limited to polyoxyethylene sorbitan oleate, polyoxyethylene sorbitan monooleate, Polysorbate 80, Tween™ 80, Canarcel™ TW 80, Atlox™ 1087, Alkest™ 80 and Crillet™ 4.

In at least one embodiment, the ratio by weight of the first non-ionic surfactant to the second non-ionic surfactant is from about 90:10 to about 80:20. In at least one embodiment, the ratio by weight of the first non-ionic surfactant to the second non-ionic surfactant is about 90:10. In at least one embodiment, the ratio by weight of the first non-ionic surfactant to the second non-ionic surfactant is about 85:15. In at least one embodiment, the ratio by weight of the first non-ionic surfactant to the second non-ionic surfactant is about 83:17. In at least one embodiment, the co-emulsifier has a combined HLB of from about 4 to about 10. In at least one embodiment, the co-emulsifier has a combined HLB of from about 6 to about 9. In at least one embodiment, the co-emulsifier has a combined HLB of from about 6 to about 7.

In at least one embodiment, the antimicrobial composition further comprises a carrier fluid. The carrier fluid is a water-miscible liquid and, in at least one embodiment, is selected from water, glycols and mixtures thereof. Suitable glycols include but are not limited to ethylene glycol, diethylene glycol, triethylene glycol, propylene glycol, dipropylene glycol, tripropylene glycol, and monoethers or polyethers thereof. In at least one embodiment, the antimicrobial composition comprises from about 25% to about 70% by weight of the carrier fluid, such that the solid content of the antimicrobial composition is about 30% to about 75% by weight. In at least one embodiment, the antimicrobial composition comprises from about 35% to about 65% by weight of the carrier fluid, such that the solid content of the antimicrobial composition is about 35% to about 65% by weight. In at least one embodiment, the antimicrobial composition comprises from about 45% to about 60% by weight of the carrier fluid, such that the solid content of the antimicrobial composition is about 40% to about 55% by weight.

In at least one embodiment, the antimicrobial composition further comprises a defoaming agent. In at least one embodiment the defoaming agent comprises at least one of silicones and paraffinic mineral oils. Suitable defoaming agents are well known to the skilled person and are available commercially from suppliers including but not limited to BYK Additives and Instruments, Air Products, and the Dow Chemical Company. In at least one embodiment, the antimicrobial composition comprises from about 0.3% to about 3% by weight of the defoaming agent. In at least one embodiment, the antimicrobial composition comprises from about 0.3% to about 1% by weight of the defoaming agent.

In at least one embodiment, the antimicrobial composition is prepared by blending the components to form a stable emulsion, as will be understood by one skilled in the art. In at least one embodiment, a mixture of IPBC and BCM, emulsifier, emulsion stabilizer, defoaming agent and water can be emulsified and the resulting emulsion can be blended with a solution of PPCZ in a glycol solvent. Alternatively, the co-emulsifier can be added to the solution of PPCZ in a glycol solvent to form a pre-mix, and the pre-mix can be incorporated into the emulsion containing the mixture of IPBC and BCM. In at least one embodiment, the glycol solvent is dipropylene glycol monomethyl ether (DPM). In at least one embodiment, the ratio by weight of the emulsion of IPBC and BCM, emulsifier, emulsion stabilizer, defoaming agent and water to the solution of PPCZ or to the pre-mix of the solution of PPCZ and the co-emulsifier is from about 76:24 to about 60:40.

In at least one embodiment, the mixture of IPBC and BCM, emulsifier, emulsion stabilizer, defoaming agent and water can contain about 25% to about 40% by weight of the active antimicrobial ingredients, about 10% to about 20% by weight of the emulsifier, about 4% to about 23% by weight of the emulsion stabilizer, about 0.4% to about 5% by weight of the defoaming agent and about 40% to about 60% by weight of water. In such embodiments, the ratio of IPBC: BCM in the active microbial ingredients can be from about 75:25 to about 85:15.

In at least one embodiment, the solution of PPCZ can be prepared by diluting 95% to 100% by weight PPCZ (Wocosen™ 95%, Janssen PMP or Preventol™ A 12, Lanxess) with a glycol solvent at a ratio of about 50:50 by weight. In at least one embodiment, the glycol solvent is dipropylene glycol monomethyl ether (DPM). In at least one embodiment, a co-emulsifier is added to the solution of PPCZ to form the pre-mix. In at least one embodiment, a first non-ionic surfactant and a second non-ionic surfactant are added individually to the solution of PPCZ to form the pre-mix. In at least one embodiment, the pre-mix can contain about 7% to about 8% by weight of the first non-ionic surfactant, about 1% to about 2% by weight of the second non-ionic surfactant and about 43% to about 46% by weight PPCZ.

In at least one alternative embodiment, the antimicrobial composition is prepared by blending one or more pre-formed antimicrobial components, each containing one or more of the active antimicrobial ingredients. In at least one embodiment, one or more of the pre-formed antimicrobial components further contain one or more emulsion stabilizers, one or more emulsifiers or one or more defoaming agents. One or more other additives, including but not limited to preservatives, anti-settling agents, anticaking agents, pH stabilizers and rheology modifiers, can also be present.

In at least one embodiment, the antimicrobial composition is prepared from a mixture of about 30% to about 50% by weight of an aqueous dispersion containing about 30-50% by weight IPBC and about 5-20% by weight kaolin, about 20% to about 35% by weight of an aqueous dispersion containing about 1-10% by weight IPBC, about 5-20% by weight kaolin and about 10-20% by weight carbendazim, and about 24% to about 40% by weight of a solution containing about 45-50% by weight propiconazole in a glycol solvent. In at least one embodiment, the antimicrobial composition further contains about 3.0% to about 3.5% by weight of a co-emulsifier comprising a first non-ionic surfactant and a second non-ionic surfactant.

In at least one embodiment, the antimicrobial composition is prepared from a mixture of about 37% to about 42% by weight of an aqueous dispersion containing about 40% by weight IPBC and about 5-20% by weight kaolin (Polyphase™ PW 40, Troy Corporation), about 25% to about 30% by weight of an aqueous dispersion containing about 5% by weight IPBC, about 5-20% by weight kaolin and about 15% by weight carbendazim (Polyphase™ P678, Troy Corporation), about 2.2% to about 2.9% by weight of a first non-ionic surfactant (Span™ 80, Croda), about 0.3% to about 0.7% by weight of a second non-ionic surfactant (Tween™ 80, Croda), and about 29% to about 33% by weight of a technical concentrate containing about 45-50% by weight propiconazole in a glycol solvent (Wocosen™ 50TK, Janssen PMP or Preventol™ A 12-TK 50, Lanxess), or a solution of PPCZ prepared by diluting 95% to 100% by weight PPCZ (Wocosen™ 95%, Janssen PMP or Preventol™ A 12, Lanxess) with a glycol solvent at a ratio by weight of about 50:50, as described herein.

In at least one embodiment, about 57% to about 61% by weight of Polyphase™ PW 40 and about 39% to about 43% by weight of Polyphase™ P678 can be mixed together to form an emulsion. In at least one embodiment, about 90% to about 92% by weight of Preventol™ A 12-TK 50 or a solution of PPCZ prepared by diluting Preventol™ A 12 with DPM at a ratio of about 50:50 can be mixed with about 7% to about 8% by weight of Span™ 80 and about 1% to about 2% by weight of Tween™ 80 to form a pre-mix. In at least one embodiment, about 32% to about 36% by weight of the premix can be added to about 64% to about 68% by weight of the emulsion to form the antimicrobial composition.

The present antimicrobial composition can be diluted with water for application to freshly cut and undried (green) wood surfaces, including but not limited to green lumber or timber, rough cut logs and rough sawn beams and planks. Such application can provide temporary protection to the green wood surfaces during natural drying and before further machining. In at least one embodiment suitable for dilution with water, the present antimicrobial composition advantageously contains a co-emulsifier.

In at least one embodiment suitable for application to green wood surfaces, the present antimicrobial composition can be diluted with water at a ratio of antimicrobial composition to water of from about 1:44 (v/v) to about 1:17 (v/v). In at least one embodiment, the ratio of antimicrobial composition to water can be from about 1:37 (w/w) to about 1:14 (w/w). In at least one embodiment, the diluted antimicrobial composition comprises from about 1.0% by weight of active ingredients to about 2.5% by weight of active antimicrobial ingredients. The skilled person will be able to determine and select a suitable dilution ratio for a particular application depending on factors including but not limited to the dimensions of the wood to be protected, the amount of sapwood or heartwood, the initial moisture content of the wood, the environmental conditions under which the wood is stored, and the time of natural drying or exposure to seasoning. For example, large logs or beams intended for construction of cabins or log homes and often containing high proportions of sapwood may require application of a diluted antimicrobial composition containing a concentration of active antimicrobial ingredients as high as 2.5% by weight to prevent attack by deep penetrating blue stain fungi or surface-growing black and green mold fungi which are hard to remove. As an additional example, thinner rough sawn lumber intended for further cutting or shaping may be adequately protected by application of a diluted antimicrobial composition containing a concentration of active antimicrobial ingredients as low as 1.0% by weight.

The present antimicrobial composition can be used in the preparation of an antimicrobial wood preservative. In at least one embodiment, the antimicrobial composition can be formulated with one or more additives to prepare an antimicrobial wood preservative concentrate, as will be understood by the skilled person. Suitable additives are well known in the art and include but are not limited to carriers, resins, UV additives to provide protection from UV-induced degradation, water-repellent additives and the like. In at least one embodiment, the antimicrobial composition can be incorporated into a pre-formed wood preservative formulation, to prepare an antimicrobial wood preservative or an antimicrobial wood preservative concentrate.

In at least one embodiment, the antimicrobial wood preservative concentrate contains about 3% to about 5% by weight of total active antimicrobial ingredients (IPBC, PPCZ and BCM). In at least one embodiment, the antimicrobial wood preservative concentrate can be diluted with water to prepare the antimicrobial wood preservative, which, in at least one embodiment, is suitable for application to a wood surface to be preserved. In at least one embodiment, the ratio of antimicrobial wood preservative concentrate to water in the antimicrobial wood preservative is from 1:4 to 1:25 by volume. In at least one embodiment, the ratio of antimicrobial wood preservative concentrate to water is about 1:6 by volume. In at least one embodiment, the ratio of antimicrobial wood preservative concentrate to water is about 1:9 by volume. The skilled person will be able to determine and select a suitable dilution ratio depending on factors including but not limited to the desired or required uptake of preservative into the wood to be treated, the conditions of use (including but not limited to the ease with which the wood absorbs liquids, and the extent of direct contact of the wood with the ground), the seasonal conditions, the extent of exposure of the wood to moderate or harsh conditions, including but not limited to UV exposure, the risk of leaching of active ingredients and the risk of fungal attack to the wood to be treated.

The antimicrobial wood preservative can be applied to a wood surface to be preserved by any application method known in the art, including but not limited to spraying, dipping or immersion, flooding, or impregnation. Dip or immersion treatments can be used to protect green wood or dried construction elements, and include but are not limited to dipping in dipping tanks for 1 to 5 minutes or immersion for 5 to 60 seconds. Flood treatments can be used to protect construction and framing wood, shingles, sheathing and wood composite elements. Impregnation treatments include but are not limited to impregnation in hermetically closed treating vessels, including but not limited to double vacuum treatment, vacuum-pressure-vacuum treatment and full-cell vacuum-pressure treatment. When impregnating wood in a hermetically closed treating vessel, the wood can be treated with an antimicrobial wood preservative prepared by diluting the present antimicrobial wood preservative concentrate with water at a ratio by volume of from about 1:12 to about 1:25, such that about 3 kg to about 12 kg of dried active material is retained per $m^3$ of wood. Double vacuum treatment can be used to treat wood joinery, windows and doors. Vacuum-pressure-vacuum treatment can be used to treat construction wood in ground contact. Full-cell vacuum-pressure treatment can be used to treat wood exposed to harsh conditions, in humid areas and/or in ground contact, such that about 7 kg to about 12 kg of dried active material is retained per $m^3$ of wood. The person skilled in the art will be able to select and carry out an appropriate application method for the specific conditions.

In at least one embodiment, the present antimicrobial composition can be incorporated into a compatible water-based wood coating to form an antimicrobial water-based wood coating product. Such water-based coatings are desirable for use because of their lower environmental and health risks, and the ease of cleaning of tools used to apply the coating. It can be difficult to formulate such water-based wood coatings with known antimicrobial compounds, which often have low solubility in water, and therefore are difficult to mix effectively with water-based coatings. Because the present antimicrobial composition is a water-miscible stable emulsion of the active antimicrobial ingredients, it can be easier to formulate and can generally be more readily mixed with water-based coatings.

As used herein, the term "compatible water-based wood coating" is intended to mean a water-based wood coating into which the antimicrobial composition can be incorporated, such that the resulting antimicrobial wood coating product is suitable for use in coating wood. The person of skill in the art can readily determine the compatibility of the antimicrobial composition with other components in the water-based coating.

In use, incorporation of the antimicrobial composition into the compatible water-based wood coating can take place at any convenient phase of the coating production process, including but not limited to the grinding phase or the letdown phase. Alternatively, the antimicrobial composition can be added to the prepared compatible water-based coating once production is complete. In at least one embodiment, the antimicrobial composition can be mixed with the wood coating and the mixture agitated or stirred to form the antimicrobial wood coating product. In at least one embodiment, the mixture is stirred for at least 5 minutes. In at least one embodiment, the wood coating is stirred or agitated prior to addition of the antimicrobial composition, and the antimicrobial composition is mixed with the wood coating in the letdown phase.

In at least one embodiment, the antimicrobial wood coating product comprises from about 0.25% to about 2.50% by weight of the antimicrobial composition. Such embodiments of the antimicrobial wood coating product can comprise from about 0.06% to about 1.2% by weight of total active antimicrobial ingredients. In at least one embodiment, the antimicrobial wood coating product can comprise from about 0.09% to about 1.0% by weight of total active antimicrobial ingredients.

In at least one embodiment, the antimicrobial wood coating product comprises from about 0.25% to about 1.00% by weight of the antimicrobial composition. Such embodiments of the antimicrobial wood coating product are useful for application to wood surfaces in interior locations. In at least one embodiment, the antimicrobial wood coating product comprises from about 1.00% to about 2.50% by weight of the antimicrobial composition. Such embodiments of the antimicrobial wood coating product are useful for application to wood surfaces in exterior locations. In at least one embodiment, the antimicrobial wood coating product comprises about 0.25%, about 0.50%, about 1.00%, about 1.50%, about 2.00% or about 2.50% by weight of the antimicrobial composition. The antimicrobial wood coating product can be applied to a wood surface by any application method known to the skilled person.

In at least one embodiment, the present antimicrobial composition has antifungal or fungicidal properties, and can be used to prepare a fungicidal wood preservative or a fungicidal wood coating product, as described herein. In such embodiments, the fungicidal wood preservative or wood coating product is effective to kill, or to prevent or reduce growth of or infection by, one or more fungi which infect, damage or otherwise attack wood. Such fungi include but are not limited to surface molds, blue stain fungi and wood rotting fungi. In at least one embodiment, the fungicidal wood preservative or wood coating product is effective to kill, or to prevent or reduce growth of or infection by, a plurality of fungi which attack wood. In such embodiments, the fungicidal wood preservative or wood coating product can have broad spectrum activity against a range of wood attacking fungi.

Non-limiting examples of wood attacking fungi which can be killed or controlled by antimicrobial wood preservatives and/or wood coating products containing the present antimicrobial composition include wood discoloring organisms, deep penetrating wood staining fungi and surface growing mold fungi, including but not limited to *Ceratocystis pilifera, Aureobasidium pullulans, Aspergillus niger, Sclerophoma pityophila, Trichoderma viride, Penicillium citrinum, Alternaria alternate, Alternaria tenuissima, Cladosporium cladosporioides, Cladosporium herbarum, Chaetomium globosum, Stachybotrys chartarum,* and *Stachybotrys atra*; and wood destroying fungi, including white and brown rot species, including but not limited to *Coniophora puteana, Coniophora cerebella, Postia placenta, Serpula lacrymans, Gloeophyllum trabeum, Trametes versicolor, Pleurotus ostreatus,* and *Stereum hirsutum.*

In at least one embodiment, the present antimicrobial composition shows an increased efficacy against one or more species of microorganisms, including but not limited to one or more species of fungi, compared to the efficacy shown by comparable formulations containing one or two of the individual active antimicrobial ingredients, IPBC, BCM or PPCZ, alone. In at least one embodiment, the present antimicrobial composition shows an increased efficacy against one or more fungal species compared to the efficacy shown by a comparable formulation of IPBC alone. In at least one embodiment, the present antimicrobial composition shows an increased efficacy against one or more fungal species compared to the efficacy shown by a comparable formulation of IPBC and BCM alone. In at least one embodiment, the present antimicrobial composition shows an increased efficacy against one or more fungal species compared to the efficacy shown by a comparable formulation of PPCZ alone.

Without being bound by theory, it is believed that when at least one embodiment of an antimicrobial wood coating product containing the present antimicrobial composition is applied to a wood surface, the active ingredients can migrate into the wood cells near the surface, preventing microorganisms from growing on the coating film or on the surface of the wood under the coating film. The growth of these microorganisms, while not necessarily causing decay or structural damage to the wood, can cause an unsightly "blotchy" appearance below the coating film, which can considerably reduce the commercial value of the wooden structure. In addition, the adhesion of the coating to the wood can be compromised by the microbial growth such that, in some cases, the coating can peel away from the wood. With reference to FIG. 1, it is believed that when at least one embodiment of a wood coating 12 containing the present antimicrobial composition is applied to wood 10, the antimicrobial components can penetrate into the wood for some distance (about 0.5 mm to about 2 mm) before the coating film dries. This is believed to provide a protective zone 14 under coating 12, which provides added protection to the coated surface. Thus, even if the uncoated side or rear surfaces 16 of the wood are invaded by wood staining fungi, the coated surface of the wood is protected from discoloration and peeling away of the coating. Such wood staining fungi include but are not limited to species such as *Aureobasidium pullulans*, which may not cause decay or loss of mechanical strength in the wood, but can cause unsightly discoloration and loss of adhesion of the coating.

In at least one embodiment, the antimicrobial composition can advantageously prevent or reduce bacterial contamination of a water-based wood coating to which the antimicrobial composition is added, thus providing an antimicrobial wood coating product with improved storage time without the need for additional in-can preservatives. Bacteria growing in water-based wood coatings or preservatives can cause problems such as unpleasant or offensive odours, reduction of solid content, a decrease in adhesion of the dried film after application, and degradation of antifungal compounds, with consequent loss of antifungal efficacy. Thus, the antimicrobial wood coating product, in at least one embodiment, can be stored for a longer period of time with reduced or minimal bacterial contamination than a comparable water-based wood coating which does not contain the present antimicrobial composition. Antimicrobial wood coating products containing the present antimicrobial composition have been found to show no detectable bacterial growth after extended storage for up to 12 months under normal ambient and increased (for example, 32° C.) temperatures.

EXAMPLES

Other features of the present invention will become apparent from the following non-limiting examples which illustrate, by way of example, the principles of the invention.

Example 1

An antimicrobial composition according to the present invention was incorporated into a water-repellent, UV resistant wood preservative formulation to provide an antimicrobial wood preservative concentrate comprising 3.33% by weight of active antimicrobial ingredients (IPBC, BCM and PPCZ). A negligible amount of blue pigment was added to facilitate visualization of treated surfaces. The concentrate was subsequently diluted with water at ratios of 6:1, 9:1 and 25:1 (water:concentrate, v/v) to provide test formulations A, B and C, respectively.

Five-inch sapwood sections cut from lodgepole pine 2×4" studs (Shelburne Wood Protection Ltd.) were end-sealed to prevent longitudinal penetration, immersed for 10 seconds in one of test formulations A, B or C and allowed to dry for 10 days under ambient conditions (21° C., 50% relative humidity). The sealed ends of the blocks were cut-removed to expose untreated surfaces as a control, and the blocks were exposed to mold species (*Aureobasidium pullulans* ATCC (American Type Culture Collection) 9348; *Aspergillus niger* ATCC 6275 and *Penicillium* sp ATCC 9849) for 12 weeks in a humidity chamber under a controlled environment (28° C.-32° C., 95%-98% relative humidity) as described in ASTM Standard D3273-12 (2012), Standard Test Method for Resistance to Growth of Mold on the Surface of Interior Coatings in an Environmental chamber, ASTM International, West Conshohocken, Pa. Three replicate samples were treated with each test formulation. The results are presented in Table 1 below.

TABLE 1

| Test formulation | Dilution ratio | Concentration of active ingredients (%, w/w) | Preservative absorption (retention of actives) (g/m²) | Average mold growth on wood surfaces (%) |
|---|---|---|---|---|
| A | 6:1 | 0.476 | 118 (0.562) | 0 |
| B | 9:1 | 0.333 | 123 (0.409) | 0 |
| C | 25:1 | 0.128 | 127 (0.163) | 0 |
| untreated | N/A | N/A | 0.00 | 50 |

Figure 2:
FIG. 2 is a photograph of lodgepole pine wood blocks treated with an antimicrobial wood preservative according to the present invention, and tested for mold growth in a controlled environment mold growth chamber.

As seen in FIG. 2, no mold growth was observed on the treated surfaces, even those treated with the most dilute formulation C, while the untreated exposed surface was intensively colonized by mold. Some discoloration of the treated wood was observed due to chemical reactions, and was not the result of fungal attack.

Example 2

Figure 3:
FIG. 3 is a photograph of a typical attic in the Lower Mainland of British Columbia which has been attacked by mold as a result of condensation due to high ambient relative humidity conditions (photo courtesy of RDH Building Engineering Ltd.)

An independent comparative test of mold control products from Canadian suppliers, including the test formulation A described in Example 1 above (Product A), was carried out, at the request of a Canadian provincial government agency (BC Housing Homeowner Protection Office), to identify products from a variety of manufacturers which might be useful for preventing mold growth on wood roof sheathing in ventilated attics of wood frame structures in British Columbia. As seen in FIG. 3, unprotected attics in this region are susceptible to attack by mold fungi.

The test was carried out according to AWPA Standard E24-12 (Standard Method of Evaluating the Resistance of Wood Product Surfaces to Mold Growth; published May 1, 2012 by American Wood Protection Association). The identities of the products tested were kept confidential, and made known only to their particular manufacturers.

Test samples of Douglas fir plywood sheets with one side of sapwood-predominant veneer, having dimensions of 160 mm×65 mm×10 mm, were treated with each product according to manufacturer's specifications. In the case of present Product A, 20 test samples were immersed vertically for 5 seconds, removed, turned upside down and immersed again for an additional 5 seconds, then allowed to dry for at least 10 days. The 10 samples with the most similar uptake were selected for use in the test. The average uptake of Product A was 137 g/m², with an average uptake of active antimicrobial ingredients of 0.65 g/m². Uptake values for other products tested (unidentified) varied from 106 to 259 g/m². Samples were subjected to the test conditions described in AWPA Standard E24-12, and were randomly assigned to locations in the test chamber. Fungal inocula contained five common mold organisms, namely *Alternaria tenuissima* (Forintec 691B); *Aspergillus niger* (Forintec 207F); *Aureobasidium pullulans* (Forintec 132F); *Penicillium citrinum* (Forintec 595F); and *Cladosporium cladosporioides* (Forintec 273C). Mold growth was monitored and reported at 2, 4, 6 and 8 weeks. Samples were rated for mold growth on a scale 0 to 5 where 0 represents no growth and 5 represents intensive fungal growth. The results are provided in Table 2 below.

TABLE 2

| | Mold growth rating | | | | | | | |
|---|---|---|---|---|---|---|---|---|
| | 2 weeks | | 4 weeks | | 6 weeks | | 8 weeks | |
| Product | Average (standard deviation) | Range (max-min) | Average (standard deviation) | Range (max-min) | Average (standard deviation) | Range (max-min) | Average (standard deviation) | Range (max-min) |
| 1 | 0.0 (0) | 0-0 | 0.8 (0.8) | 2-0 | 2.3 (1.3) | 4-1 | 3.0 (0.8) | 4-2 |
| 2 | 0.2 (0.4) | 1-0 | 3.6 (0.7) | 4-2 | 4.0 (0) | 4-4 | 4.0 (0) | 4-4 |

TABLE 2-continued

| | Mold growth rating | | | | | | | |
|---|---|---|---|---|---|---|---|---|
| | 2 weeks | | 4 weeks | | 6 weeks | | 8 weeks | |
| Product | Average (standard deviation) | Range (max-min) | Average (standard deviation) | Range (max-min) | Average (standard deviation) | Range (max-min) | Average (standard deviation) | Range (max-min) |
| 3 | 0.1 (0.3) | 1-0 | 0.4 (0.5) | 1-0 | 1.1 (1.0) | 3-0 | 2.3 (1.2) | 4-1 |
| 4 | 0.0 (0) | 0-0 | 0.9 (0.7) | 2-0 | 3.1 (1.0) | 4-1 | 3.8 (0.4) | 4-3 |
| 5 | 0.0 (0) | 0-0 | 1.1 (0.6) | 2-0 | 3.1 (0.9) | 4-2 | 4.0 (0.5) | 5-3 |
| 6 (Product A) | 0.1 (0.3) | 1-0 | 0.1 (0.3) | 1-0 | 1.0 (0.5) | 2-0 | 2.4 (0.7) | 3-1 |
| 7 | 0.0 (0) | 0-0 | 0.6 (0.5) | 1-0 | 2.7 (0.7) | 4-2 | 3.8 (0.4) | 4-3 |
| 8 | 0.0 (0.3) | 1-0 | 2.4 (1.1) | 4-1 | 4.0 (0) | 4-4 | 4.0 (0) | 4-4 |
| 9 | 0.4 (0.5) | 1-0 | 3.7 (0.7) | 4-2 | 4.0 (0) | 4-4 | 4.2 (0.4) | 5-4 |
| 10 | 0.0 (0) | 0-0 | 0.0 (0) | 0-0 | 0.1 (0.3) | 1-0 | 0.1 (0.3) | 1-0 |

As seen from the results in Table 2, Product A (table entry 6) showed excellent control of mold growth under the test conditions, and was identified along with the product of table entry 3 (unidentified) as providing the best resistance to mold growth among the products tested. The product of table entry 10 is a non-commercial 100% concentrated multi-active formulation developed by the independent organization conducting the test (FPInnovations, Vancouver, BC, Canada), and was included as a positive control.

The three commercial products which provided the best resistance to mold growth in the test above (table entries 1, 3 and 6 (Product A)) were further tested under modified conditions which incorporate intermittent vapour condensation on sample surfaces to better represent the conditions typically found in attics in the Lower Mainland of British Columbia. Ten test samples were prepared as described above, and the five samples with the most similar uptake were selected for use in the test. The average uptake of Product A was 141.2 g/m², while the average uptake of table entries 1 and 3 were 154.6 g/m² and 113.2 g/m², respectively. Fungal inocula were as described above.

The conditions and apparatus described in AWPA Standard E24-12 were used, with some modification. The treated samples were placed in holes cut in an insulated flat roof, rather than being suspended inside the chamber, so that the sapwood-predominant veneer test face of the sample was exposed to the interior of the chamber and the other face was exposed to the outside of the chamber. The interior of the chamber was maintained at 100% humidity and 25° C., and the air outside the chamber was conditioned to 16° C. to 20° C., so that condensation on the test samples was promoted. A fan installed in the chamber could be operated to blow air from the chamber outwards through an 8 cm by 9 cm hole in the chamber wall, and a similar hole at the other end of the chamber allowed entry of air from outside the chamber while the fan was operating. When the fan was not operating, plastic hinged flaps prevented air from entering or leaving the chamber.

The test samples were exposed to a cycle including a condensation period of three days and a drying period of four days to provide an accelerated simulation of attic conditions. The condensation period included a repeated cycle of a 30 minute chamber condition of about 26° C. and 96% relative humidity, followed by a 30 minute period where cooler room air was introduced into the chamber by means of the fan, to provide a chamber condition of about 22° C. and 75% relative humidity. With entry of cooler air, water inside the chamber was heated to raise the temperature inside the chamber to 26° C. once operation of the fan was discontinued. When the three day condensation period had ended, the heater and fan were turned off to allow the chamber to slowly equilibrate to ambient temperature (about 20° C. to 22° C.) and about 80% to 90% relative humidity over the four day drying period.

Mold growth on test samples was observed at 2, 4, 6, 8 and 12 weeks of exposure, and rated as follows:
0 No visible growth;
1 Mold covering up to 10% of surfaces, providing growth is not so intense or colored as to obscure the sample color over more than 5% of surfaces;
2 Mold covering between 10% and 30% of surfaces, providing growth is not so intense or colored as to obscure the sample color over more than 10% of surfaces;
3 Mold covering between 30% and 70% of surfaces, providing growth is not so intense or colored as to obscure the sample color over more than 30% of surfaces;
4 Mold on greater than 70% of surfaces, providing growth is not so intense or colored as to obscure the sample color over more than 70% of surfaces;
5 Mold covering 100% of surfaces or with less than 100% coverage and with intense or colored growth obscuring greater than 70% of the sample color.

The results are presented in Table 3 below, and in FIG. 4.

TABLE 3

| | 2 Weeks | | 4 Weeks | | 6 Weeks | | 8 Weeks | | 12 Weeks | |
|---|---|---|---|---|---|---|---|---|---|---|
| Test sample | Avg* (SD) | Max-min | Avg* (SD) | Max-min | Avg* (SD) | Max-min | Avg* (SD) | Max-min | Avg* (SD) | Max-min |
| Positive control (untreated Douglas fir plywood) | 4.0 (0.7) | 5-3 | 4.8 (0.4) | 5-4 | 4.8 (0.4) | 5-4 | 4.8 (0.4) | 5-4 | 5.0 (0.0) | 5-5 |

TABLE 3-continued

| Test sample | 2 Weeks Avg* (SD) | 2 Weeks Max-min | 4 Weeks Avg* (SD) | 4 Weeks Max-min | 6 Weeks Avg* (SD) | 6 Weeks Max-min | 8 Weeks Avg* (SD) | 8 Weeks Max-min | 12 Weeks Avg* (SD) | 12 Weeks Max-min |
|---|---|---|---|---|---|---|---|---|---|---|
| Positive control (untreated Ponderosa pine sapwood) | 1.6 (1.8) | 4-0 | 1.6 (1.8) | 4-0 | 1.6 (1.8) | 4-0 | 2.0 (1.9 | 4-0 | 2.6 (2.1) | 5-0 |
| Entry 1 | 0.0 (0.0) | 0-0 | 0.2 (0.4) | 1-0 | 0.2 (0.4) | 1-0 | 0.8 (1.3) | 3-0 | 1.4 (1.5) | 3.0 |
| Entry 3 | 0.6 (0.9) | 2-0 | 0.2 (0.4) | 1-0 | 0.2 (0.4) | 1-0 | 0.0 (0.0) | 0-0 | 0.0 (0.0) | 0-0 |
| Entry 6 (Product A) | 0.0 (0.0) | 0-0 | 0.0 (0.0) | 0-0 | 0.0 (0.0) | 0-0 | 0.0 (0.0) | 0-0 | 0.0 (0.0) | 0-0 |

*Average (standard deviation); average of 5 replicates

Figure 4:
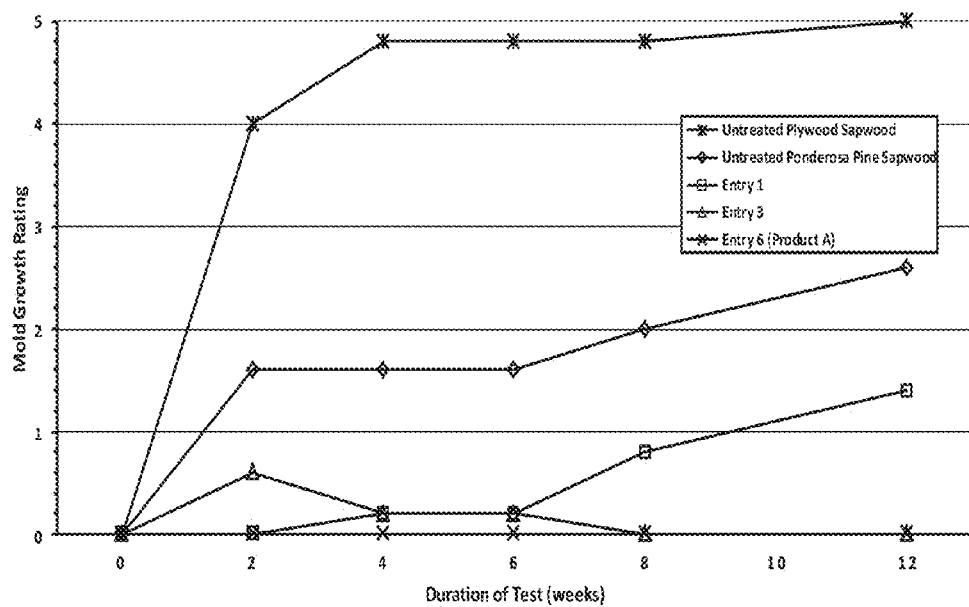
FIG. 4 is a chart showing the degree of mold growth under simulated attic conditions on Douglas fir plywood blocks treated with an antimicrobial wood preservative according to the present invention, treated with other products or untreated, or on untreated Ponderosa pine sapwood blocks.

As seen from the data in Table 3 and FIG. 4, Product A (entry 6 of Table 2) provided the best control of mold growth of the three products tested, and prevented mold growth under the test conditions for at least 12 weeks.

Example 3

An antimicrobial composition according to the present invention was incorporated into a wood preservative formulation to provide an antimicrobial wood preservative concentrate comprising 3.33% by weight of active antimicrobial ingredients (IPBC, BCM and PPCZ). The concentrate was diluted with water at a ratio of 12:1 (water:formulation, v/v), to provide test formulation D, containing 0.26% of active antimicrobial ingredients. Comparative formulation E containing 0.26% of IPBC was prepared similarly.

White pine sapwood blocks (20 mm×10 mm×6 mm) were immersed for 5 seconds in test formulation D or in the comparative formulation E, and were allowed to dry without contacting each other for 10 days under controlled laboratory conditions (21° C., 40-50% relative humidity). The treated blocks were sterilized by passing briefly through an alcohol based burner flame, and were placed directly on sterile Difco™ culture medium containing 3.5% malt extract agar in plastic culture dishes (100 mm in diameter, 20 mm in height; 5 replicates each).

The culture medium was inoculated as close to the dish edge as possible with two inocula (approximately 10 mm×10 mm fragments) of each of three decay fungi, namely *Gloeophyllum trabeum* GT RR-5 (brown rot fungus), *Postia placenta* (brown rot fungus) and *Trametes versicolor* (white rot fungus) (6 inocula in total per plate). *Gloeophyllum trabeum* GT RR-5 was initially isolated from a naturally infected log placed out of ground contact, and the culture was purified by multiple mycelia transfer using beer-based medium (Sansin) containing 3% malt extract, 2% agar and 0.3% food-grade 35% hydrogen peroxide ($H_2O_2$). *Postia placenta* and *Trametes versicolor* are isolates obtained from the Faculty of Forestry, University of Toronto. Poor growth of *Trametes versicolor* mats is believed to result from contamination of the originally acquired culture. Formation of fungal colonies was observed for four weeks.

Figure 5:
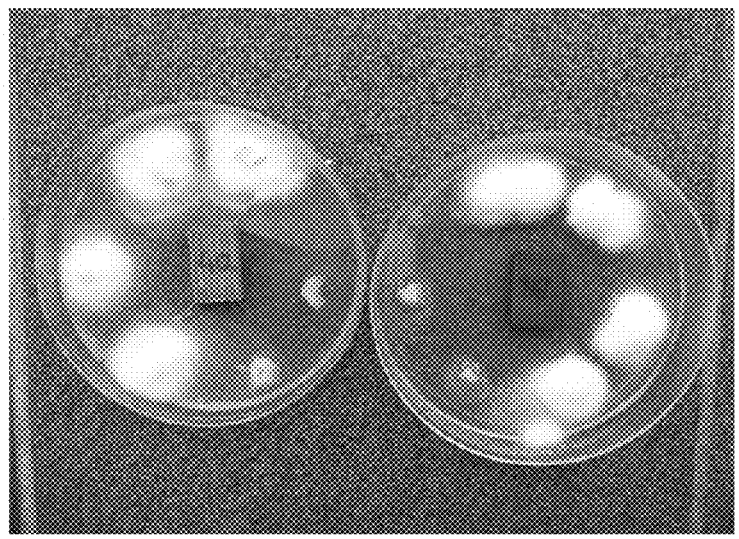
FIG. 5 is a photograph showing zones of inhibition of growth of decay fungi around white pine sapwood blocks treated with an antimicrobial wood preservative according to the present invention or with a wood preservative containing 3-iodo-2-propynyl N-butyl carbamate (IPBC) alone (photo: The Sansin Corporation)

No wood blocks were observed to be colonized by fungal mycelia. Typical results are seen in FIG. 5, in which sample 16 (right), which was treated with test formulation D, shows a larger zone of growth inhibition than does sample 40 (left), which was treated with IPBC alone (comparative formulation E). Average growth inhibition zones were measured at 1 to 12 mm for the blocks treated with IPBC alone (comparative formulation E) and 7 to 15 mm for test formulation D. *Gloeophyllum trabeum* appeared to be the most tolerant of the three species tested to the antifungal effects of both test formulation D and IPBC alone.

Example 4

An antimicrobial composition according to the present invention was incorporated into an alkyd-based, water-dilutable, clear decorative wood stain to provide an antimicrobial wood coating formulation containing 0.28% by weight of active antimicrobial ingredients (IPBC, BCM and PPCZ) (formulation F). A comparable wood coating formulation was prepared containing 0.28% of IPBC alone (formulation G). White pine sapwood blocks (50 mm×25 mm×15 mm) were individually dip treated for 5 seconds with formulation F or formulation G, dried for 2 days and acclimatized for 7 days at 80% humidity. The thickness of the dry film on coated surfaces was measured at 1 to 1.3 mils.

The blocks were sterilized by promptly passing the blocks over an alcohol burner flame. Ten replicate culture plates were prepared by placing a block treated with formulation F, a block treated with formulation G and a control untreated block on sterile 2 cm×2 cm plastic supports in each of ten plastic culture dishes (100 mm in diameter, 20 mm in height) containing sterile Difco™ culture medium comprising 3% malt extract agar. The dishes were aseptically sprayed with either a spore suspension containing a blend of spores of *Aspergillus niger* (strain ATTC 6275) and *Penicillium funiculosum* (strain ATTC 11797), or with a spore suspension containing spores of *Aureobasidium pullulans* (strain ATTC 9348). The plates were incubated at 28° C. for four weeks and the growth of fungal mycelia was rated as follows:

0—No growth;

1—Traces of growth (up to 10% visible surface overgrown);

2—Light growth (10 to 30% visible surface covered);

3—Moderate growth (30 to 60% visible surface covered);

4—Heavy growth (more than 60% covered to complete coverage).

Figure 6:
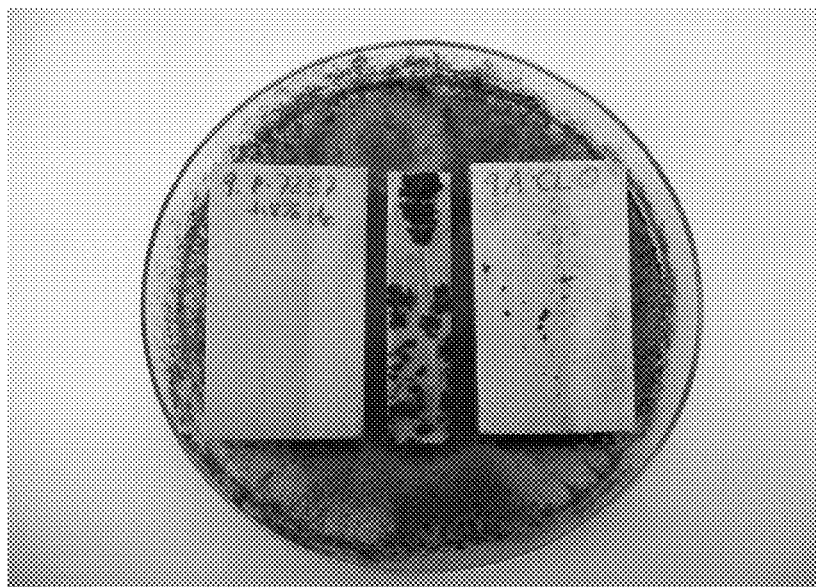
FIG. 6 is a photograph showing the degree of mold growth on white pine sapwood blocks which are uncoated or coated with a clear wood coating containing an antimicrobial composition according to the present invention or IPBC alone (the lid of the culture dish was removed for the photograph; photo: The Sansin Corporation)

The results are presented in Table 4 and typical results are shown in FIG. 6.

TABLE 4

Fungal Growth Ratings:

| Dish number | Formulation G (IPBC) | Control sample (untreated) | Formulation F (IPBC, PPCZ, BCM) |
|---|---|---|---|
| Dishes sprayed with *A. pullulans* spore suspension | | | |
| 1 | 0 | 1 | 0 |
| 2 | 1 | 1 | 0 |
| 3 | 0 | 2 | 0 |
| 4 | 0 | 1 | 0 |
| 5 | 1 | 2 | 0 |
| Dishes sprayed with *A. niger* and *P. funiculosum* spore suspension | | | |
| 6 | 0 | 3 | 0 |
| 7 | 1 | 3 | 0 |
| 8 | 1 | 3 | 0 |
| 9 | 3 | 4 | 0 |
| 10 | 0 | 2 | 0 |

As can be seen from FIG. 6 (photograph taken with the lid removed from the culture dish), the block coated with formulation F (left, indicated as "9 P-7257") showed no mold growth, the block coated with the coating containing IPBC alone (formulation G, right, indicated as "9A CLO") showed limited mold growth, and the untreated control block (FIG. 6, center, unmarked) showed significant mold growth.

Example 5

Wood preservative formulations containing an antimicrobial composition according to the present invention were tested (at the Earth Science Center, Faculty of Forestry, University of Toronto) for resistance to wood decay fungi by the NWWDA standard Soil Block Test Method (NWWDA Standard TM1:1994 (R2006) (1994, renewed 2006), National Wood Window and Door Association). An antimicrobial composition according to the present invention was incorporated into a ready to use wood preservative formulation to provide an antimicrobial wood preservative formulation comprising 0.46% by weight of active antimicrobial ingredients (IPBC, BCM and PPCZ) (formulation H). Formulation H was diluted 5.4 times with water to provide formulation I, containing 0.085% active antimicrobial ingredients (IPBC, BCM and PPCZ).

Formulation H and formulation I were applied to 19 mm blocks of red pine sapwood and poplar sapwood and the blocks were vacuum treated for 30 minutes as described in section 9 of the NWWDA standard method. The average retention (six replicates) for the treated red pine sapwood blocks was 1.8 kg/m$^3$ (for blocks treated with formulation H) and 0.31 kg/m$^3$ (for blocks treated with formulation I), and, for the treated poplar sapwood blocks, the average retention was 1.5 kg/m$^3$ (for blocks treated with formulation H) and 0.29 kg/m$^3$ (for blocks treated with formulation I). A set of treated red pine sapwood blocks were exposed to accelerated leaching as described in Method B of the NWWDA standard method. Untreated blocks were used as a control and each test was carried out with six replicate blocks.

After conditioning and weighing, the test blocks were sterilized overnight by exposure to UV light and were placed in glass jars on feeder strips pre-inoculated with brown rot fungus (*Gloeophyllum trabeum*) (red pine sapwood blocks) or white rot fungus (*Trametes versicolor*) (poplar sapwood blocks). The blocks were incubated for 12 weeks, then re-equilibrated and weighed. The results are shown in Table 5.

TABLE 5

| Test fungus | Formulation | Active (%, w/w) | Leaching | Weight loss (%) | Standard deviation |
|---|---|---|---|---|---|
| Brown rot fungus | H | 0.46 | Non-leached | −0.1 | 1.0 |
| (*Gloeophyllum* | H | 0.46 | Leached | 0.6 | 0.7 |
| *trabeum*) | I | 0.085 | Non-leached | 5.8 | 2.7 |
| (red pine sapwood) | I | 0.085 | Leached | 2.9 | 0.3 |
| | Untreated | 0 | Non-leached | 38.6 | 7.8 |
| White rot fungus | H | 0.46 | Non-leached | 0.1 | 1.0 |
| (*Trametes* | I | 0.085 | Non-leached | 22.9 | 10.8 |
| *versicolor*) | Untreated | 0 | Non-leached | 46.0 | 10.4 |
| (poplar sapwood) | | | | | |

Figure 7:
FIG. 7 is a photograph showing the degree of fungal growth on untreated red pine sapwood cubes and red pine sapwood cubes treated with an antimicrobial wood preservative according to the present invention and exposed to brown rot fungus (photo courtesy of the Earth Science Center, Faculty of Forestry, University of Toronto)

As seen from the results in Table 5, untreated (control) red pine sapwood blocks had a significant average weight loss of 38.6% due to decomposition caused by *Gloeophillum trabeum*. However, treated red pine sapwood blocks showed minimal weight loss when treated with either formulation H or formulation I. Even after leaching, minimal weight loss was observed, indicating that the active ingredients were well retained. In addition, as seen in FIG. 7, a block (blue, right) treated with formulation I and exposed to *Gloeophillum trabeum* for 12 weeks showed minimal colonization, even when exposed to fungal mycelia directly placed on top of the block. An untreated control block (left) showed extensive colonization.

In addition, untreated poplar sapwood blocks also showed significant weight loss of 46% when exposed to *Trametes versicolor*. However, poplar sapwood samples treated with formulation H lost only 0.1% of their initial weights. Poplar wood samples treated with formulation I showed a weight loss of 22.9%.

Example 6

The experiment was carried out at the Earth Science Center, Faculty of Forestry, University of Toronto. Formulation H (Example 5) was applied to twelve (25 mm×25 mm×25 mm) red pine sapwood cubes using a 30-minute vacuum treatment at a pressure of 100 mm Hg, according to the NWWDA standard Soil Block Test Method (NWWDA Standard TM1:1994 (R2006) (1994, renewed 2006), National Wood Window and Door Association). The blocks were dried for two weeks under ambient laboratory conditions and placed individually in small beakers. Six of the blocks were loaded with weights and subjected to leaching by immersion in distilled water (approximately nine times the volume of the block samples) at room temperature for two hours and drying overnight at 49° C., repeated daily for 14 days. Three of the six leached blocks and three of the six unleached blocks were precisely cut-dissected along a longitudinal direction at 5 mm increments. The remaining three of the six leached blocks and three of the six unleached blocks were precisely cut-dissected along a radial direction at 5 mm increments. All sections were individually ground to 30 mesh particle size and extracted with methanol in an ultrasonic bath for 3 hours. The methanol extracts were analyzed for presence of actives (IPBC, PPCZ and BCM) using high performance liquid chromatography (HPLC), at a limit of quantification of 0.02 μg/ml. The results (average of three replicates per treatment) are presented in Table 6 and in FIGS. 8A and 8B.

TABLE 6

| Sample | Block section (mm) | Leaching | Retention of Actives μg/g$_{wood}$ | % |
|---|---|---|---|---|
| Radial sections | | | | |
| 1-NL | 0-5 | Non-leached | 3,295 | 0.33 |
| 2-NL | 5-10 | Non-leached | 1,277 | 0.13 |
| 3-NL | 10-15 | Non-leached | 376 | 0.04 |
| 4-NL | 15-20 | Non-leached | 1,744 | 0.17 |
| 5-NL | 20-25 | Non-leached | 2,328 | 0.23 |
| 1-L | 0-5 | Leached | 3,473 | 0.35 |
| 2-L | 5-10 | Leached | 997 | 0.10 |
| 3-L | 10-15 | Leached | 694 | 0.07 |
| 4-L | 15-20 | Leached | 1,464 | 0.15 |
| 5-L | 20-25 | Leached | 2,850 | 0.29 |
| Longitudinal sections | | | | |
| 1-NL | 0-5 | Non-leached | 7,417 | 0.74 |
| 2-NL | 5-10 | Non-leached | 656 | 0.07 |
| 3-NL | 10-15 | Non-leached | 286 | 0.03 |
| 4-NL | 15-20 | Non-leached | 524 | 0.05 |
| 5-NL | 20-25 | Non-leached | 5,241 | 0.52 |
| 1-L | 0-5 | Leached | 6,844 | 0.68 |
| 2-L | 5-10 | Leached | 453 | 0.05 |
| 3-L | 10-15 | Leached | 531 | 0.05 |
| 4-L | 15-20 | Leached | 975 | 0.10 |
| 5-L | 20-25 | Leached | 4,303 | 0.43 |

Figure 8A:
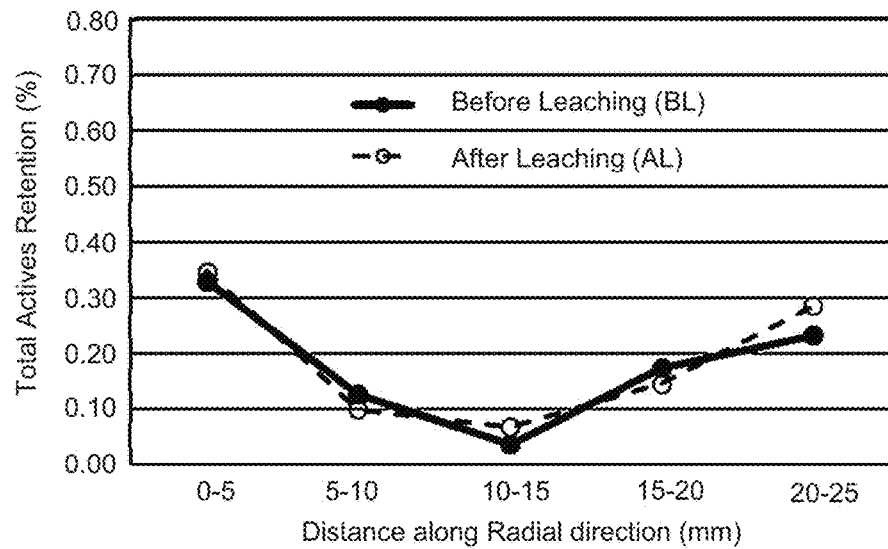
FIG. 8A is a graph showing the average retention gradient of total active ingredients along the radial direction (end to end) of red pine sapwood cubes treated with an antimicrobial wood preservative according to the present invention before and after leaching (data courtesy of the Earth Science Center, Faculty of Forestry, University of Toronto)
Figure 8B:
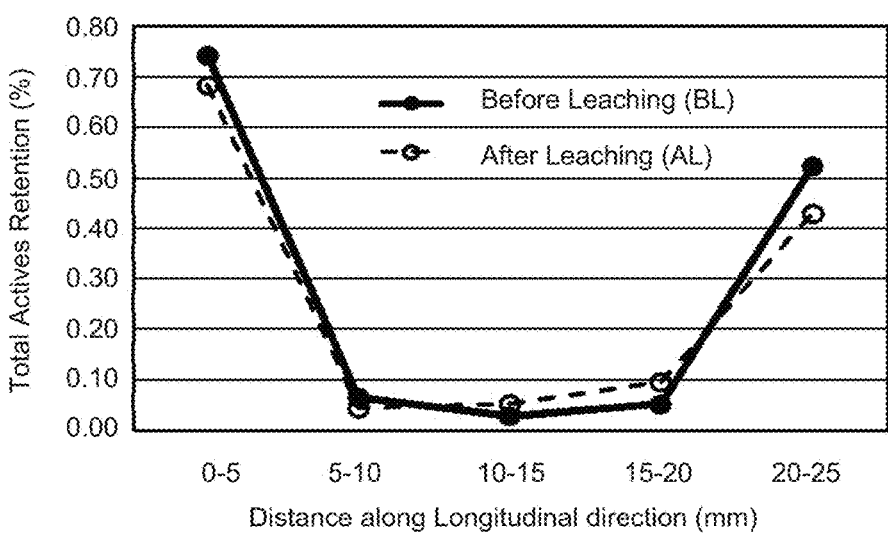
FIG. 8B is a graph showing the average retention gradient of total active ingredients along the longitudinal direction (end to end) of red pine sapwood cubes treated with an antimicrobial wood preservative according to the present invention before and after leaching (data courtesy of the Earth Science Center, Faculty of Forestry, University of Toronto)

As can be seen from the results in Table 6 and FIGS. 8A and 8B, no significant loss of active ingredients was observed from the leached blocks compared to the non-leached blocks.

Example 7

Wooden 2×4 studs (Douglas fir, 8 feet in length, green or kiln dried) were flood treated in a test retort by a commercial wood preservation company under industrial conditions with test formulations A, B, C and D, prepared by diluting the antimicrobial wood preservative concentrate of Example 1 comprising 3.33% by weight of active antimicrobial ingredients (IPBC, BCM and PPCZ) with water at ratios of 6:1, 9:1, 25:1 and 12:1, respectively (Examples 1 and 3). Five-inch long samples cut from the treated studs were tested for mold resistance using the AWPA E24-2012 test method (Example 2), along with untreated control samples of Southern yellow pine sapwood or black or white spruce. The samples were continuously exposed to mold species for 8 weeks at 95% relative humidity and temperatures of 28° C. to 32° C. Mold growth was visually assessed and recorded at 2, 4, 6 and 8 weeks exposure time, and was rated as follows:

0 No visible growth;

1 Mold covering up to 10% of surfaces, with mild mycelia density, obscuring hardly 5% surface;

2 Mold covering between 10-30% of surfaces, with mild mycelia density, obscuring up to 10% surface;

3 Mold covering between 30-70% of surfaces, with medium mycelia density, obscuring up to 30% surface;

4 Mold covering greater than 70% of surfaces, with intense mycelia density, obscuring up to 70% surface;

5 Mold covering 100% of surface with intense discoloration, obscuring more than 70% surface.

The results are presented in Table 7.

TABLE 7

| Sample number | Wood Species and Treatment | Test Formulation (dilution) | Percentage of sapwood (%) | Ratings | | | |
|---|---|---|---|---|---|---|---|
| | | | | Two Weeks | Four Weeks | Six Weeks | Eight Weeks |
| I-19 | Southern | Untreated | 100 | 3 | 3 | 4 | 5 |
| I-20 | yellow pine | control | 100 | 3 | 4 | 5 | 5 |
| I-21 | sapwood | | 100 | 3 | 3 | 4 | 5 |
| | Average (standard deviation) | | | 3.0 (0.0) | 3.3 (0.6) | 4.3 (0.6) | 5.0 (0.0) |
| II-15 | Black Spruce | Untreated | Unknown | 0 | 0 | 1 | 1 |
| II-16 | | control | Unknown | 0 | 0 | 1 | 1 |
| II-17 | White Spruce | Untreated | Unknown | 0 | 0 | 2 | 3 |
| II-18 | | control | Unknown | 1 | 1 | 2 | 4 |
| | Average (standard deviation) | | | 0.3 (0.5) | 0.3 (0.5) | 1.5 (0.6) | 2.3 (1.5) |
| III-1 | DouglasFir | A (6:1) | 3 | 0 | 0 | 0 | 0 |
| III-2 | (green) | | 3 | 0 | 0 | 0 | 0 |
| III-3 | DouglasFir | | 50 | 0 | 0 | 0 | 0 |
| III-4 | (kiln dried) | | 50 | 0 | 0 | 0 | 0 |
| | Average (standard deviation) | | | 0.0 (0.0) | 0.0 (0.0) | 0.0 (0.0) | 0.0 (0.0) |
| IV-5 | DouglasFir | B (9:1) | 60 | 0 | 0 | 2 | 2 |
| IV-6 | (green) | | 60 | 0 | 0 | 3 | 3 |
| IV-7 | DouglasFir | | 5 | 0 | 0 | 2 | 2 |
| IV-8 | (kiln dried) | | 5 | 0 | 0 | 1 | 1 |
| | Average (standard deviation) | | | 0.0 (0.0) | 0.0 (0.0) | 2.0 (0.8) | 2.0 (0.8) |
| V-9 | Douglas Fir | D (12:1) | 0 | 0 | 0 | 0 | 0 |
| V-10 | (green) | | 0 | 0 | 0 | 0 | 0 |
| V-11 | Douglas fir | | 60 | 0 | 0 | 1 | 1 |
| | (kiln dried) | | | | | | |

TABLE 7-continued

| Sample number | Wood Species and Treatment | Test Formulation (dilution) | Percentage of sapwood (%) | Ratings | | | |
|---|---|---|---|---|---|---|---|
| | | | | Two Weeks | Four Weeks | Six Weeks | Eight Weeks |
| | Average (standard deviation) | | | 0.0 (0.0) | 0.0 (0.0) | 0.3 (0.6) | 0.3 (0.6) |
| VI-12 | Douglas Fir | C (25:1) | 0 | 0 | 0 | 0 | 0 |
| VI-13 | (green) | | 0 | 0 | 0 | 0 | 0 |
| VI-14 | Douglas fir (kiln dried) | | 2 | 0 | 0 | 0 | 0 |
| | Average (standard deviation) | | | 0.0 (0.0) | 0.0 (0.0) | 0.0 (0.0) | 0.0 (0.0) |

Figure 9A:
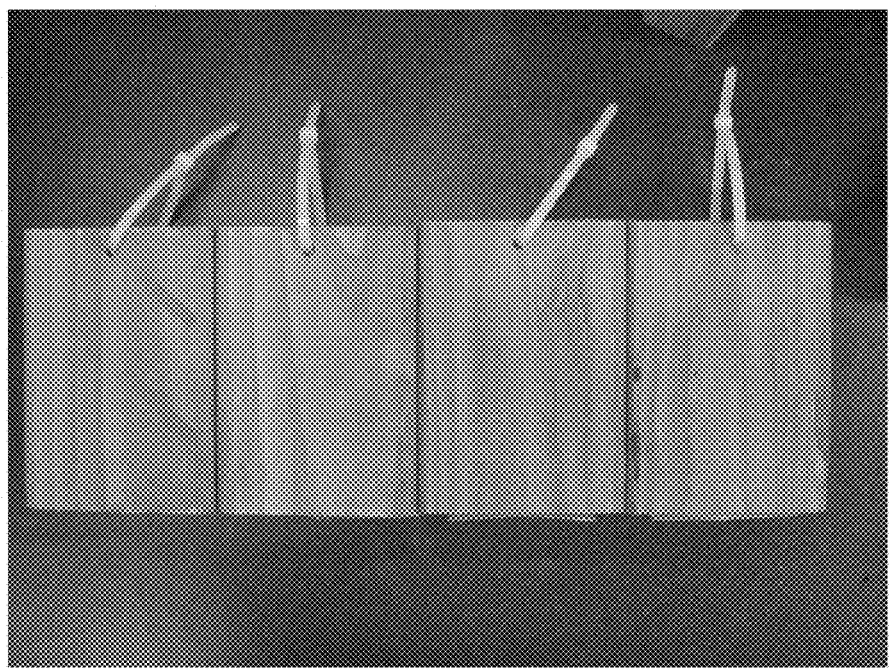
FIG. 9A is a photograph of blocks cut from Douglas fir studs treated with an antimicrobial wood preservative according to the present invention, and tested for mold growth (photo courtesy of the Earth Science Center, Faculty of Forestry, University of Toronto)
Figure 9B:
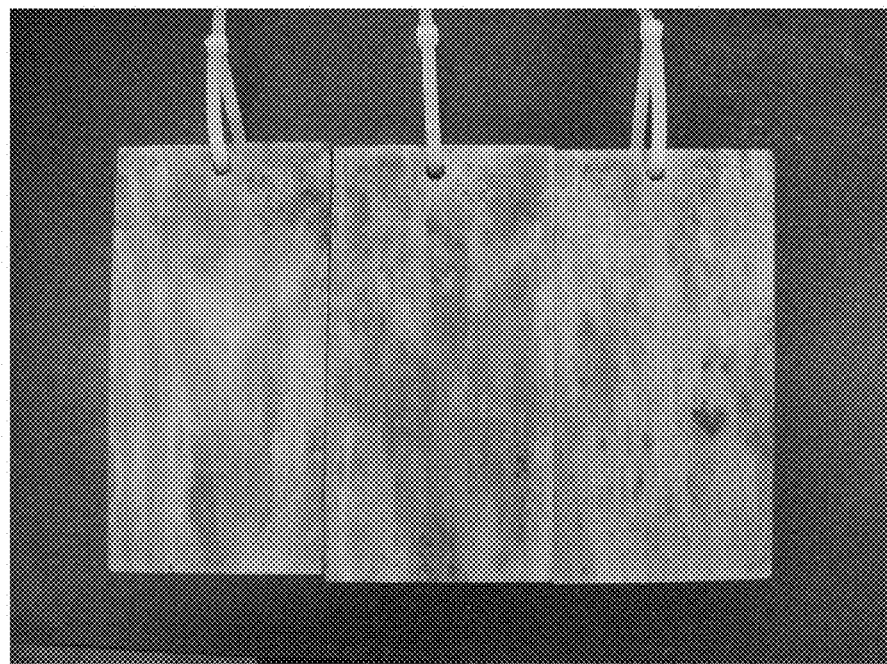
FIG. 9B is a photograph of untreated Southern yellow pine sapwood blocks tested for mold growth (photo courtesy of the Earth Science Center, Faculty of Forestry, University of Toronto)

As seen from the results in Table 7 and as shown in FIG. 9A, test formulation A, containing the antimicrobial wood preservative concentrate at a dilution ratio of 6:1, protected treated stud samples having up to 50% sapwood content completely from mold colonization over an exposure period of 8 weeks. In contrast, as seen in FIG. 9B, untreated Southern yellow pine sapwood blocks were extensively colonized by mold under the same conditions. As well, the present antimicrobial wood preservative concentrate showed moderate to good protection, even at a dilution of 12:1, against mold growth in studs containing up to 60% sapwood over an exposure period of 8 weeks. The stud samples treated with test formulation C (containing the antimicrobial wood preservative concentrate at a 25:1 dilution ratio) showed no mold growth, but contained a very high percentage of heartwood, which is more naturally resistant to mold infection than is sapwood.

Example 8

The minimum inhibitory concentration (MIC) of total active ingredients (IPBC, PPCZ and BCM) in an antimicrobial composition according to the present invention (test formulation J) against a number of wood-discoloring or wood-destroying fungi was determined using the Spiral Plater method as known in the art and compared against the MIC of total active ingredients in comparative formulations containing only IPBC (comparative formulation K, Polyphase™ PW 40, Troy Corporation) or a mixture of IPBC and BCM (1:3 ratio by weight, comparative formulation L, Polyphase™ P678, Troy Corporation). The results are shown in Table 8.

TABLE 8

| Fungus | Test Formulation J (IPBC, PPCZ, BCM) | Comparative Formulation K (IPBC) | Comparative Formulation L (IPBC, BCM) |
|---|---|---|---|
| Mold (wood-discolouring) fungi | | | |
| Cladosporium cladosporioides (ATCC #16022) | <17 ppm | <19 ppm | 24 ppm |
| Aspergillus niger (ATCC #6275) | <17 ppm | <19 ppm | 34 ppm |
| Trichoderma viride (ATCC #20476) | <17 ppm | <19 ppm | <7 ppm |
| Wood rotting fungi | | | |
| Gloeophyllum trabeum (ATCC #11539) | <17 ppm | <19 ppm | <7 ppm |
| Postia placenta (ATCC #36334) | <17 ppm | <19 ppm | <7 ppm |
| Coniophora puteana (ATCC #36336) | <17 ppm | <19 ppm | 43 ppm |

TABLE 8-continued

| Fungus | Test Formulation J (IPBC, PPCZ, BCM) | Comparative Formulation K (IPBC) | Comparative Formulation L (IPBC, BCM) |
|---|---|---|---|
| Trametes versicolor (ATCC #42462) | <17 ppm | <19 ppm | 43 ppm |

As seen from the results presented in Table 8, the present antimicrobial composition exhibited MIC values against the fungi tested which are at least comparable to those of comparative formulations K and L, and exhibited MIC values against two commercially important black mold species (*Cladosporium cladosporioides* and *Aspergillus niger*) and two decay fungi (*Coniophora puteana* and *Trametes versicolor*) which are superior to those of comparative formulation L.

Example 9

The experiment was carried out at the Earth Science Center, Faculty of Forestry, University of Toronto. An antimicrobial composition according to the present invention was incorporated into a water-repellent, UV resistant wood preservative formulation to provide an antimicrobial wood preservative concentrate comprising 3.33% by weight of active antimicrobial ingredients (IPBC, BCM and PPCZ, Example 1). The concentrate was subsequently diluted with water at a ratio of 6:1 (water:concentrate, v/v) to provide test formulation M containing 0.476% by weight of total active ingredients (IPBC, PPCZ and BCM). The biocidel properties of test formulation M were compared to those of comparative formulation N (similar to test formulation M but containing 0.476% by weight of IPBC only), comparative formulation O (similar to test formulation M but containing 0.476% by weight of a mixture of IPBC and BCM at a 1:3 ratio by weight) and comparative formulation P (similar to test formulation M but containing 0.476% by weight of PPCZ only). Each of formulations M, N, O and P was further diluted with water to provide test solutions containing 900 μg/mL, 500 μg/mL, 250 μg/mL, 100 μg/mL, 50 μg/mL or 12.5 μg/mL of total active ingredients.

A total of 10 Southern yellow pine sapwood samples cut from parent boards comprising on average 5 to 10 annual rings per inch were immersed in the test solutions for 3 minutes, followed by brushing to cover any untreated areas. The samples were allowed to dry for 15 days at ambient laboratory conditions and five samples having the closest preservative uptake were selected for testing according to the AWPA E24-12 standard mold exposure test (Example 2). Untreated control samples were immersed in water for 3 minutes and allowed to dry for 15 days. Samples were suspended in the humidity chamber, four inches above a soil bed inoculated with *Aureobasidium pullulans, Aspergillus niger, Penicillium* sp and *Alternaria tenuissima*. Samples were observed for mold growth at 2, 4, 6, 8 and 10 weeks exposure, and were rated as follows:
- 0—No growth;
- 1—Mold covering up to 10% of surfaces;
- 2—Mold covering between 10 to 30% of surfaces;
- 3—Mold covering between 30 to 70% of surfaces;
- 4—Mold covering greater than 70% of surfaces;
- 5—Mold covering 100% of surfaces with intense color.

The results are shown in Table 9:

TABLE 9

| Formulation | Dilution (Conc. of total active ingredients) (μg/mL) | Average retention of active ingredients (μg/cm$^2$) | Mold growth rating (average of 5 replicates) | | | | |
|---|---|---|---|---|---|---|---|
| | | | 2 weeks | 4 weeks | 6 weeks | 8 weeks | 10 weeks |
| Untreated controls | N/A (0.0) | 0.0 | 2.2 | 3.4 | 4.6 | 4.8 | 5.0 |
| Test Formulation M | 373:1 (12.5) | 0.4 | 0.0 | 2.8 | 3.0 | 3.4 | 3.4 |
| Comparative Formulation N | | 0.4 | 00 | 2.8 | 3.2 | 3.6 | 3.8 |
| Comparative Formulation O | | 0.6 | 0.0 | 2.6 | 3.2 | 3.6 | 4.0 |
| Comparative Formulation P | | 0.5 | 0.0 | 3.2 | 3.4 | 3.6 | 4.0 |
| Test Formulation M | 93:1 (50) | 2.5 | 0.0 | 2.2 | 3.0 | 3.4 | 3.4 |
| Comparative Formulation N | | 2.1 | 0.0 | 2.4 | 3.4 | 3.6 | 3.8 |
| Comparative Formulation O | | 1.8 | 0.0 | 3.0 | 3.2 | 3.4 | 3.4 |
| Comparative Formulation P | | 1.8 | 0.0 | 2.8 | 3.2 | 3.6 | 3.6 |
| Test Formulation M | 47:1 (100) | 4.0 | 0.0 | 1.4 | 2.4 | 2.4 | 2.6 |
| Comparative Formulation N | | 3.3 | 0.0 | 1.6 | 2.2 | 2.6 | 2.8 |
| Comparative Formulation O | | 3.0 | 0.0 | 2.2 | 2.6 | 2.8 | 2.8 |
| Comparative Formulation P | | 2.8 | 0.0 | 2.6 | 2.8 | 3.0 | 3.0 |
| Test Formulation M | 19:1 (250) | 7.6 | 0.0 | 1.4 | 1.8 | 2.2 | 2.2 |
| Comparative Formulation N | | 6.9 | 0.0 | 1.2 | 2.0 | 2.4 | 2.4 |
| Comparative Formulation O | | 7.0 | 0.0 | 2.0 | 2.0 | 3.0 | 3.0 |
| Comparative Formulation P | | 5.8 | 0.0 | 2.0 | 2.4 | 3.4 | 3.6 |
| Test Formulation M | 9:1 (500) | 17.4 | 0.0 | 1.0 | 1.4 | 1.6 | 2.0 |
| Comparative Formulation N | | 15.8 | 0.0 | 1.0 | 1.2 | 1.4 | 2.6 |
| Comparative Formulation O | | 16.8 | 0.0 | 1.2 | 1.4 | 1.6 | 2.4 |
| Comparative Formulation P | | 13.5 | 0.0 | 1.4 | 2.8 | 3.4 | 3.6 |
| Test Formulation M | 5:1 (900) | 32.5 | 0.0 | 0.6 | 1.2 | 1.4 | 1.4 |
| Comparative Formulation N | | 29.2 | 0.0 | 0.6 | 1.0 | 1.4 | 1.6 |
| Comparative Formulation O | | 26.9 | 0.0 | 0.4 | 1.8 | 2.0 | 2.2 |
| Comparative Formulation P | | 24.7 | 0.0 | 1.2 | 2.2 | 2.4 | 2.8 |

Figure 10A:
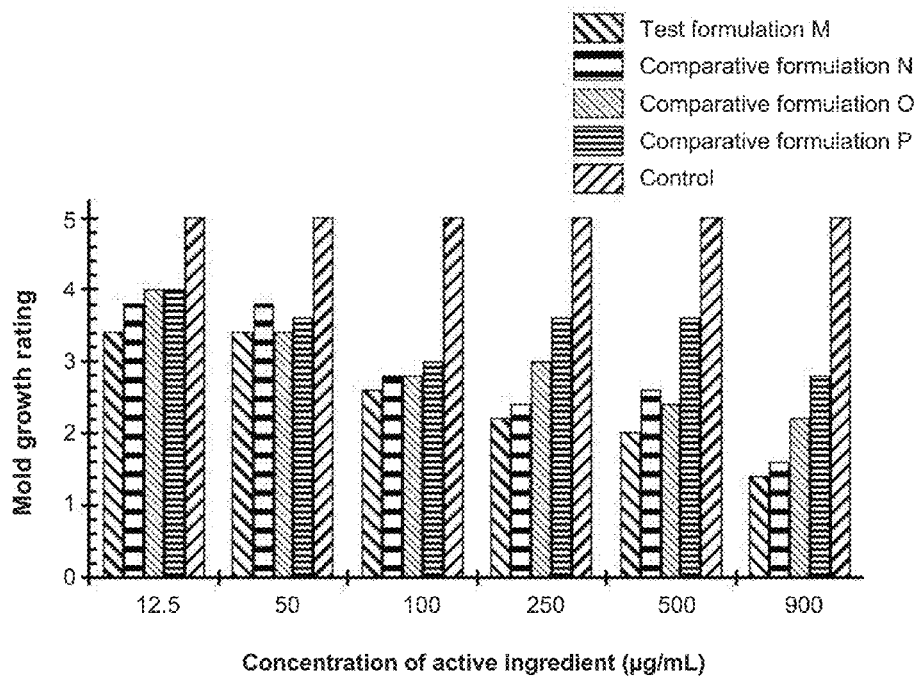
FIG. 10A is a chart showing the degree of mold growth on Southern yellow pine sapwood samples treated with an antimicrobial wood preservative according to the present invention, treated with other products or untreated (data courtesy of the Earth Science Center, Faculty of Forestry, University of Toronto)
Figure 10B:
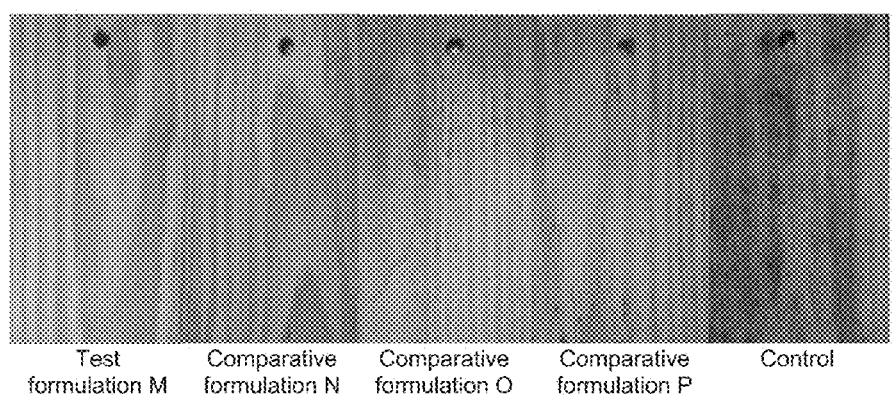
FIG. 10B is a photograph showing the degree of fungal growth on Southern yellow pine sapwood samples untreated or treated with an antimicrobial wood preservative according to the present invention or with a comparative formulation containing IPBC, IPBC and BCM, or PPCZ, at a concentration of active ingredients of 900 µg/ml, and tested for mold growth (photo courtesy of the Earth Science Center, Faculty of Forestry, University of Toronto).

As seen in Table 9 and FIG. 10A, test formulation M showed better control of mold growth than any of the comparative formulations N, O or P after 10 weeks of exposure, especially at concentrations of 250 μg/mL to 900 μg/mL. In contrast, untreated control samples were completely overgrown by test fungi after this exposure time, as can be seen at the right side of FIG. 10B.

The embodiments described herein are intended to be illustrative of the present compositions and methods and are not intended to limit the scope of the present invention. Various modifications and changes consistent with the description as a whole and which are readily apparent to the person of skill in the art are intended to be included. The appended claims should not be limited by the specific embodiments set forth in the examples, but should be given the broadest interpretation consistent with the description as a whole.

The invention claimed is:

1. An antimicrobial composition comprising:
about 10% to about 25% by weight of 3 iodo-2-propynyl N-butyl carbamate (IPBC);

about 12% to about 20% by weight of propiconazole;
about 2% to about 8% by weight of carbendazim;
about 2% to about 4% by weight of a co-emulsifier, wherein the co-emulsifier comprises a first non-ionic surfactant and a second non-ionic surfactant, wherein the first non-ionic surfactant has a lower hydrophilic-lipophilic balance (HLB) than the second non-ionic surfactant; and
about 25% to about 70% by weight of a carrier fluid;
wherein the antimicrobial composition is in the form of a suspoemulsion wherein the IPBC and the carbendazim are present in solid form and are dispersed in the antimicrobial composition as finite particles and wherein the propiconazole is provided as a solution in a glycol solvent.

2. The antimicrobial composition according to claim 1, further comprising about 7% to 15% by weight of an emulsifier.

3. The antimicrobial composition according to claim 2 wherein the emulsifier comprises an anionic surfactant.

4. The antimicrobial composition according to claim 2 wherein the emulsifier comprises a non-ionic surfactant.

5. The antimicrobial composition according to claim 1, wherein the ratio by weight of the first non-ionic surfactant to the second non-ionic surfactant is from about 90:10 to about 80:20, and the co-emulsifier has a combined HLB of from about 4 to about 10.

6. The antimicrobial composition according to claim 1, further comprising about 3% to about 14% by weight of an emulsion stabilizer.

7. The antimicrobial composition according to claim 6, wherein the emulsion stabilizer is kaolin.

8. The antimicrobial composition according to claim 1, wherein the carrier fluid is selected from water, glycols, and mixtures thereof.

9. The antimicrobial composition according to claim 1, further comprising from about 0.3% to about 3% by weight of a defoaming agent.

10. A method of preparing an antimicrobial wood coating product, the method comprising:
adding the antimicrobial composition according to claim 1 to a water-based wood coating to form a mixture; and
agitating the mixture to form the antimicrobial wood coating product.

11. The method of claim 10, wherein the antimicrobial wood coating product comprises from about 0.25% to about 2.50% by weight of the antimicrobial composition.

12. An antimicrobial wood coating product comprising a water-based wood coating and the antimicrobial composition according to claim 1.

13. The antimicrobial wood coating product according to claim 12, comprising from about 0.25% to about 2.50% by weight of the antimicrobial composition.

14. An antimicrobial composition comprising:
about 10% to about 25% by weight of 3 iodo-2-propynyl N-butyl carbamate (IPBC);
about 12% to about 20% by weight of propiconazole;
about 2% to about 8% by weight of carbendazim;
about 7% to 15% by weight of an emulsifier;
about 3% to about 14% by weight of an emulsion stabilizer;
about 0.3% to about 3% by weight of a defoaming agent;
about 2% to about 4% by weight of a co-emulsifier, wherein the co-emulsifier comprises a first non-ionic surfactant and a second non-ionic surfactant, and wherein the first non-ionic surfactant has a lower hydrophilic-lipophilic balance (HLB) than the second non-ionic surfactant; and
about 25% to about 70% by weight of a carrier fluid;
wherein the antimicrobial composition is in the form of a suspoemulsion wherein the IPBC and the carbendazim are present in solid form and are dispersed in the antimicrobial composition as finite particles and wherein the propiconazole is provided as a solution in a glycol solvent.

15. The antimicrobial composition according to claim 14, wherein the ratio by weight of the first non-ionic surfactant to the second non-ionic surfactant is from about 90:10 to about 80:20 and the co-emulsifier has a combined HLB of from about 4 to about 10.

16. An antimicrobial wood coating product comprising a water-based wood coating and the antimicrobial composition according to claim 14.

17. A method of preventing bacterial contamination of a water-based wood coating product, the method comprising adding an effective amount of the antimicrobial composition of claim 1 to the water-based wood coating product.

18. A method of preventing bacterial contamination of a water-based wood coating product, the method comprising adding an effective amount of the antimicrobial composition of claim 14 to the water-based wood coating product.

19. The antimicrobial composition according to claim 1 wherein the finite particles have a particle size from about 0.1 μm to about 10 μm or from about 10 μm to about 35 μm.

20. The antimicrobial composition according to claim 14 wherein the finite particles have a particle size from about 0.1 μm to about 10 μm or from about 10 μm to about 35 μm.

* * * * *

UNITED STATES PATENT AND TRADEMARK OFFICE
CERTIFICATE OF CORRECTION

| | | |
|---|---|---|
| PATENT NO. | : 10,201,160 B2 | Page 1 of 1 |
| APPLICATION NO. | : 15/312549 | |
| DATED | : February 12, 2019 | |
| INVENTOR(S) | : Eric Bos and Nenad Vidovic | |

It is certified that error appears in the above-identified patent and that said Letters Patent is hereby corrected as shown below:

On the Title Page

At Item (73), delete "Boss Holdings Inc." and insert --Bos Holdings Inc.--.

Signed and Sealed this
Fifth Day of May, 2020

Andrei Iancu
*Director of the United States Patent and Trademark Office*